United States Patent [19]

Eckberg

[11] Patent Number: 5,412,133

[45] Date of Patent: May 2, 1995

[54] RADIATION ACTIVE SILICON COMPOUNDS HAVING THIOETHER LINKED FUNCTIONAL GROUPS

[75] Inventor: Richard P. Eckberg, Saratoga Springs, N.Y.

[73] Assignee: General Electric Company, Waterford, N.Y.

[21] Appl. No.: 956,924

[22] Filed: Oct. 5, 1992

Related U.S. Application Data

[60] Division of Ser. No. 700,073, May 3, 1991, abandoned, which is a continuation of Ser. No. 235,800, Aug. 23, 1988, abandoned, which is a continuation-in-part of Ser. No. 80,723, Jul. 31, 1987, abandoned.

[51] Int. Cl.$^6$ ................................................. C07F 7/04
[52] U.S. Cl. ........................................ 556/427; 522/99; 522/172
[58] Field of Search ................... 522/99, 172; 556/427

[56] References Cited

U.S. PATENT DOCUMENTS

| | | | |
|---|---|---|---|
| 2,960,492 | 11/1960 | Morton | 556/427 |
| 3,350,437 | 10/1967 | Simmler | 528/30 |
| 3,370,076 | 2/1968 | Niederprum | 556/427 |
| 3,691,222 | 9/1972 | Wendel | 556/427 |
| 3,729,444 | 4/1973 | Bey | 528/30 |
| 3,767,690 | 10/1973 | Speier | 556/427 |
| 3,884,860 | 5/1975 | Brown | 528/30 |
| 4,269,963 | 5/1981 | Homan et al. | 556/466 |
| 4,290,869 | 9/1981 | Pigeon | 522/99 |
| 4,359,369 | 11/1982 | Takamizawa et al. | 522/99 |
| 4,595,471 | 6/1986 | Preiner et al. | 522/29 |
| 4,707,503 | 11/1987 | Itoh et al. | 522/99 |
| 4,749,803 | 6/1988 | Dowbenko et al. | 556/427 |

FOREIGN PATENT DOCUMENTS 206465 11/1984 Japan .

OTHER PUBLICATIONS

Chemical Abstract vol. 102 #16 Abst #133704d.

*Primary Examiner*—Mark A. Chapman

[57] ABSTRACT

Radiation active silicon compounds and a method of producing the same are disclosed which have functional groups selected from either or both of mercaptan or —$CHR^1=CR^1H$ joined to a silicon atom through a thioether linkage. Further disclosed are radiation curable compositions containing the radiation active silicon compounds.

7 Claims, No Drawings

RADIATION ACTIVE SILICON COMPOUNDS HAVING THIOETHER LINKED FUNCTIONAL GROUPS

This is a divisional of application Ser. No. 07/700,073 filed on May 3, 1991, now abandoned, which is a continuation of Ser. No. 07/235,800 filed on Aug. 23, 1988, now abandoned, which is a continuation in part of Ser. No. 07/080,723 filed on Jul. 31, 1987, now abandoned.

The present invention relates to radiation active silicon compounds having functional groups linked through a thioether moiety. More particularly, the present invention relates to a process for producing radiation active silicon compounds through the reaction of mercaptan with carbon unsaturation.

BACKGROUND OF THE INVENTION

Commercially viable radiation-curable silicones for different coating applications have been the goal of recent research investigations. In the course of such investigations, there have been taught epoxysilicon/-'onium catalyst systems, U.S. Pat. Nos. 4,279,717 and 4,421,904; various acrylated and methacrylated silicones, U.S. Pat. Nos. 4,348,454 and 4,558,082; perbenzoate photocatalyzed silicone terpolymers, U.S. Pat. No. 4,558,147; and mercaptan functional silicone polymers, U.S. Pat. No. 4,595,471, among others.

A radiation-curable silicone should be easy to produce, inexpensive to process, and "user friendly"; that is, present no special problems on application and cure if it is to be a commercially viable product. Seen in this light, epoxy silicones are high in cost, difficult to process, and have limited shelf stability in the presence of 'onium-type photocatalysts. Acrylated or methacrylated silicone compositions require efficient inerting of the UV-cure chamber for fast, fully developed cure. Mercaptan vinyl-type silicone UV systems have excellent shelf stability and do not require inerting but are slow to cure and difficult to produce.

It is an object of the present invention to provide a simple and convenient method to produce a UV active silicon compound having mercaptan groups, radiation sensitive unsaturated carbon bonds or both, the method being characterized by the reaction of mercaptan with carbon unsaturation.

It is another object of the present invention to produce a UV active silicon compound having mercaptan groups, radiation sensitive unsaturated carbon bonds, or both, linked to the silicon compound by a thioether group, It is yet another object of the present invention to provide a UV curable composition containing a silicon compound having mercaptan groups, radiation sensitive unsaturated carbon bonds, or both linked to the silicon compound by a thioether group.

SUMMARY OF THE INVENTION

Briefly, there is provided by the present invention a method to produce UV active silicon compounds having the steps of:

(a) adding a mercaptan of the formula:

$$HS-R-X \quad (1)$$

where R is a divalent substituted or unsubstituted hydrocarbon radical of from 1 to 12 carbon atoms, X is —OH or —COOR$^1$, and R$^1$ is —H or a substituted or unsubstituted alkyl group of from 1 to 4 carbon atoms, to a silicon bonded unsaturated hydrocarbon of the formula $$\equiv Si-R_a-CR^1=CR^1H \quad (2)$$

wherein a is 0 or 1, R and R$^1$ are given above, to produce a thioether;

(b) esterifying or transesterifying said thioether with a UV active compound having the formula:

$$Z-R-X \quad (3)$$

wherein Z is —CR$^1$=CR$^1$H, —SH or mixtures thereof, when Z is —SH, b is 1, and R$^1$, R and X are given above, with the proviso that where X is —OH in (a), it is —COOR$^1$ in (b) and where X is —COOR$^1$ in (a), it is —OH in (b).

There are further provided by this invention compounds resulting from the above method and UV curable compositions containing these compounds.

DETAILED DESCRIPTION OF THE INVENTION

Addition reactions between mercaptans and unsaturated hydrocarbons are well known and form the basis for "thiol-ene" cure of polyolefin-polymercaptan mixtures. In terms of formulas (1) and (2) the addition reaction is schematically represented by:

$$HS-R-X + \equiv Si-R_a-CR^1=CR^1H \rightarrow \equiv Si-R_a-CR^1H-CR^1H-S-R-X \quad (4)$$

producing an —X functional thioether group.

A variety of radical generators may be used to trigger this reaction, including peroxides and azo compounds. Edwards, et al., teach certain azo compounds as being superior to either peroxides or ultraviolet radiation. An example of such a preferred azo compound is azo diisobutyronitrile.

Other initiators, whose suitability for use in a particular situation can easily be ascertained by the artisan, can also be used.

Suitable mercaptans of formula (1) include mercapto-alcohols, including beta-mecaptoethanol, gamma-mercaptopropanol, 3-mercaptophenol, etc., and mercapto-carboxylic acids, including, mercaptopropionic acid, mercaptobutyric acid, 3-mercaptobenzoic acid, methyl ester of mercaptopropionic acid, etc. Of course, the least expensive materials are preferred, being beta-mercaptoethanol and mercaptopropionic acid.

Suitable silicon bonded unsaturated hydrocarbons of formula (2) include a silicon bonded vinyl group, a silicon bonded allyl group, a silicon bonded hexyl group having terminal unsaturation, a silicon bonded octyl group having terminal unsaturation as well as a conjugated or non conjugated second point of unsaturation, a silicon bonded acrylate group, a silicon bonded methacrylate group, etc. It is especially preferred herein that the unsaturated bonds of the silicon bonded hydrocarbon group do not significantly co-react in the presence of the free radical generator. The co-reaction would lead to cross-linking rather than thiol addition. Thus, silicon bonded unsaturated hydrocarbons which more readily co-react are not preferred. For example, acrylates and methacrylates contain an electron withdrawing group proximate to the unsaturated bond which make them very reactive in radical generating environments. Thus, where acrylates and methacrylates are employed some amount of initial homopolymerization must be desired or conditions must be controlled to minimize homopolymerization as compared to mercaptan addition. From the above, it is preferred herein that the silicon bonded unsaturated hydrocarbon be silicon bonded vinyl or silicon bonded allyl groups.

Regardless of the unsaturated hydrocarbon portion of formula (2), the silicon may be a simple silane, joined with oxygen to form a siloxane, or joined with oxygen and thereby silicon as a repeating unit of a polysiloxane. As a silane, siloxane or the repeating unit of a polysiloxane, the silicon bonded unsaturated hydrocarbon will have the general formula:

$$R_b^2(R_aCR^1{=}CR^1H)_cSiO_{(4-b-c)/2} \tag{5}$$

wherein $R^2$ is hydrogen or a substituted or unsubstituted hydrocarbon radical of from 1 to 12 carbon atoms, b is 0, 1, 2, or 3; c is 1, 2, 3 or 4, and R, $R^1$ and a are given above. In the case of a silane, $b+c=4$; in the case of a siloxane, $b+c$ is less than or equal to 3, and formula (5) is combined with $(4-b-c)O_{\frac{1}{2}}R^1$ units; and in the case of polysiloxane, $b+c$ is less than or equal to 3, and formula (5) is combined with other siloxane units. Other siloxane units have the formula:

$$R_d^2SiO_{(4-d)/2}$$

where d is 0, 1, 2 or 3 and $R^2$ is described above.

Of course, the aim of adding the mercaptan to the silicon bonded unsaturated hydrocarbon is to ultimately produce a means to cure or cross-link a material. Thus, the silane, siloxane or polysiloxane should have two or more unsaturated hydrocarbon groups for mercaptan addition. It is preferred for a silane or siloxane that c is 2 or greater, and for a polysiloxane that 2 or more repeating units of formula (5) be attached to each molecule. Of course, c can be 1 in the case of the silane or siloxane where, for instance, the silane or siloxane is to end cap a polymer or combine with another silane or siloxane to produce a multifunctional material. Preferred polysiloxanes herein have a viscosity between about 5 and 100,000,000 centipoise at 25° C. Especially preferred polysiloxanes are of the type used in coatings, for example, U.S. Pat. Nos. 4,448,815 and 4,617,238, assigned to the assignee of the present invention and hereby incorporated by reference. For advantageous use in curable coatings, the polysiloxane should contain from about 0.1 to about 10% by weight siloxane bonded unsaturated hydrocarbons.

The thioether addition reaction product of formula (4) is subsequently reacted in an esterification or transesterification step with a UV active compound as shown in formula (3). The UV active compound is preferably one of two groups of compounds. The first group are those compounds containing a UV active function, $-CR^1{=}CR^1H$ which include acrylic acid, acrylic acid ester, methacrylic acid, methaylic acid ester, unsaturated butyric acid, unsaturated caproic acid, allyl alcohol, hex-1-ene-6-ol, etc. The second group are those compounds containing the UV active function, —SH, which include thiol substituted carboxylic acids such as thiol substituted butyric acid, thiol substituted caproic acid and thiol substituted hydroxy compounds such as hydroxy ethyl thiol, hydroxy propyl thiol, etc.

In terms of formulas (4) and (3) the esterification or transesterification reaction proceeds as:

$$\equiv Si{-}R_a{-}CR^1H{-}CR^1H{-}S{-}R{-}X \text{ and}$$
$$Z{-}R{-}X{\rightarrow}{\equiv}Si{-}R_a{-}CHR^1H{-}CR^1H{-}S{-}R{-}X^1{-}R{-}Z+R^1OH \tag{6}$$

where all variables are given except $X^1$ which is —COO— or —OOC—. It is important to note that esterification or transesterification requires the reaction of a hydroxyl functional organic compound with a carboxylic acid or acid ester respectively. Thus, where X is —OH in formulas (1) and (4), it is —COOR$^1$ in formula (3); and where X is —COOR$^1$ in formulas (1) and (4), it is —OH in formula (3). Thus, $X^1$, the condensation product, is an ester link oriented in either of two positions depending on the foregoing.

Suitable esterification or transesterification catalysts are well known as well as solvents. Such catalysts include the titanates, such as tetrabutyltitanate, sulfuric acid, p-toluene sulfonic acid, acid ion exchange resins, or acidified clay; solvents include, for example, toluene. The reaction is ordinarily carried out at about 100° to 200° C., and most often at about 100° to 150° C.

The resultant UV active silicon compound may be incorporated into a UV curable silicon composition as a cross-linking agent, as a polysiloxane which is self cross-linking, as a polysiloxane with a cross-linking agent, or combinations of the above. For example, the silane, siloxane, or polysiloxane may be entirely mercaptan functional. In this case, a reactive co-compound having $-CR^1{=}CR^1H$ groups is necessary to provide the mercaptan with a co-reactant. Further, the silane, siloxane or polysiloxane may contain both mercaptan and $-CR^1{=}CR^1H$ groups. In this instance, a reactive co-compound is optional depending on desired properties, and $-CR^1{=}CR^1H$ group to mercaptan ratios. Also, the silane, siloxane or polysiloxane may be entirely $-CR^1{=}CR^1H$ group functional, in which case no reactive co-compound is necessary but may, of course, be added.

In a curable silicon composition while $-CR^1{=}CR^1H$ functions may self add, mercaptan functions require the presence of at least one $-CR{=}CR_1$ group for each mercaptan. Due to the tendency of $-CR^1{=}CR^1H$ groups to self add in such compositions it is preferred to have an excess of such groups, i.e. it is preferred to have at least about two $-CR^1{=}CR^1H$ groups for each mercaptan. To produce the desired number of $-CR^1{=}CR^1H$ groups in a curable silicon composition a reactive co-compound may be used. However, the silane, siloxane or polysiloxane may have both mercaptan and $-CR^1{=}CR^1H$ groups. In such case, Z may be 50 to 95% by number $-CR^1{=}CR^1H$ and 5 to 50% by number —SH. It is one aspect of the present invention that both mercaptan and $-CR^1{=}CR^1H$ groups may be more easily formed on the same molecule.

Reactive co-compound may be organic multi acrylates and methacrylates including 1,6-hexanediol diacrylates, neopentylglycol diacrylate, trimethylol propane triacrylate, cyclohexyl acrylate, etc. Further, reactive co-compound may be acrylate and methacrylate substituted polysiloxane, as disclosed in U.S. Pat. Nos. 4,348,454; 4,558,082; 4,558,147; and 4,640,967, hereby incorporated by reference. Other such co-compounds might include multialkenyls, for example, divinylbenzene or vinyl substituted polysiloxanes.

A UV active silicon compound, whether it is silane, siloxane or polysiloxane requires only a single UV active moiety in each molecule. As stated above, if the UV active silicon compound is to be a crosslinking agent or is to be crosslinked, there should be at least two active moieties on each molecule. Of course, a polysiloxane has the capacity to contain several UV active moieties on a single molecule. The number of UV active moieties on a polysiloxane is preferably the equivalent by weight to the weight of siloxane bonded unsaturated hydrocarbons present originally during manufacture and stated above to be about 0.1 to about 10% by weight.

Formulating the curable silicon composition requires that the UV active silicon compound be mixed with an effective amount of a free radical photoinitiator and if needed, a reactive co-compound and a reactive diluent. Suitable reactive diluents might include styrene, acrylamide, acrylonitrole, methyl acrylate, methyl methacrylate, 2-ethylhexyl acrylate, etc. Viscosity is to be controlled through addition of the reactive diluent, but generally it is not desirable to add more than about 25% by weight reactive diluent.

Preferred photoinitiators are disclosed by Edwards, et al., U.S. Pat. No. 3,211,705, Hatanaka, et al., U.S. Pat. No. 4,451,634 and Eckberg, et al., U.S. Pat. No. 4,558,147, hereby incorporated by reference.

Briefly, Eckberg, et al., disclose certain perbenzoate esters having the general formula:

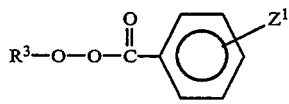

wherein $R^3$ is a monovalent alkyl or aryl group and $Z^1$ is hydrogen, alkyl, halogen, nitro, amino, or amido. The nature of the $Z^1$ substituent will affect the stability of the peroxy bond; an electron-poor substituent stabilizing the peroxy bond and an electon-rich substituent making the peroxy bond more reactive. These perbenzoate esters may be synthesized in known ways, such as by reacting benzoyl halides with hydroperoxides (see e.g. the descriptions in Blomquist and Bernstein, J. Amer. Chem. Soc., 73, 5546 [1951]). Preferred perbenzoate esters include t-butylperbenzoate and its para-substituted derivatives, t-butylper-p-nitrobenzoate, t-butylper-p-methoxybenzoate, t-butylper-p-methylbenzoate and t-butylper-p-chlorobenzoate.

In addition to t-butylperbenzoate and its derivatives as photoinitiators, Eckberg et al. disclose that the inclusion of certain photosensitizers enhances reactivity. The photosensitizers are polyaromatic compounds possessing the

chromophone, where Ph is phenyl, and having at least two benzene rings which may be fused or bridged by organic radicals or hetero-radicals such as oxa, thio and the like. Preferred photosensitizers are benzophenone, acetophenone, and t-butylanthraquinone.

Edwards, et al., teach certain azo compounds as being superior to either peroxides or ultraviolet radiation. An example of such a preferred azo compound is azo diisobutyronitrile.

Other photoinitiators, whose suitability for use in a particular situation can easily be ascertained by the artisan, can also be used, are described in U.S. Pat. Nos. 3,759,807, 3,968,305, 3,966,573, 4,113,592, 4,131,529, 4,130,600, and 4,348,462. All of these patents are incorporated by reference into the instant disclosure for their teachings related to photoinitiators.

The amount of photoinitiator employed is not critical so long as addition of the mercaptan to the unsaturated hydrocarbon is achieved. As with any catalyst, it is preferable to use the smallest effective amount possible. Generally, the amount of photoinitiator is at least one part by weight and, preferably, can be anywhere from about 1 to about 10 parts by weight based on 100 parts by weight of polysiloxane (A). More preferably, the photocatalyst level is from about 1 to about 5 parts by weight per 100 parts by weight polysiloxane (A).

As above, these compositions may be formulated for application to glass fiber, for application to paper substrates as a release coating and so on. Curing may be accomplished by simple exposure to sufficient UV radiation, augmented by final cure at room temperature or elevated temperature. Of course, the combination of elevated temperature and UV radiation exposure will produce the most rapid cure.

In order that those skilled in the art might be better able to practice the present invention, the following examples are given by way of illustration and not by way of limitation. All parts are by weight unless otherwise indicated.

Example 1

200 grams of a dimethylvinylsiloxy-stopped polydimethylsiloxane of average composition $M^{Vi}D_{20}M^{Vi}$ incorporating about 0.11 moles vinyl function per 100 grams polymer, were dispersed in 200 grams toluene with 20 grams beta-mercaptoethanol (0,256 moles). 0.21 grams of Vazo ® 88 initiator (duPont trademark for 1,1'-azobis(cyanocyclohexane)) were then added, and the complete reaction mixture agitated at 100° C. under nitrogen for 16 hours. Stripping this blend at 165° C., 20 MM Hg vacuum afforded 201 grams of a clear fluid, 80 cps viscosity. Infrared spectrum of the product showed a broad OH stretch centered at 3400 cm$^{-1}$ and the absence of vinyl peak at 1600 cm$^{-1}$. No odor of mercaptoethanol was detected in this material. 200 grams of toluene were replaced in the reaction vessel along with 0.1 g phenothiazine, 1.4 gram p-toluenesulfonic acid, and 16 gram acrylic acid (0.22 moles). This mixture was refluxed at 118° for 4 hours, with 3.4 cc H$_2$O trapped out. The acid catalyst was neutralized with 5 grams sodium bicarbonate before stripping the batch to 130°, 30 mm vacuum leaving 205 grams of a clear fluid product (after filtration), 107 cps viscosity. The infrared spectrum of this product showed a complete loss of the —OH peak and a new, intense carbonyl peak at 1738 cm$^{-1}$, indicating that the esterification had proceeded as expected.

The resultant polysiloxane was acrylic end-capped through a thioether link.

Example 2

A non-devolatilized polymer was prepared by KOH-catalyzed equilibration of cyclic tetra-dimethyl siloxane, $D_4$, cyclic tetra-methylphenylsiloxane $D_4{}^p$, cyclic tetra-methylvinylsiloxane, $D_4{}^{Vi}$, and methylvinyl chain-stopper. The mixture included 70 mole % dimethylsiloxane, 25 mole % diphenyl siloxane, and 5 mole % methylvinylsiloxane. The polymer was 582 cps viscosity, $N^D = 1.4958$ with about 0.06 moles vinyl per 100 grams polymer. 275 grams of this polymer were dispersed in 200 grams toluene with 13 grams beta-mercaptoethanol (0.166 moles), 0.75 grams Vazo ® 88 initiator, then refluxed at 100° C. under nitrogen for 18 hours. Stripping this reaction mixture at 160°, 10 mm vacuum, left 275 grams of an intermediate product, $N^D = 1.5042$, infrared spectrum consistent with addition of the SH-function to available vinyl groups. 60 grams ethylacrylate (0.6 moles) +0.3 g phenothiazine were added to the thioetheralcohol-functional phenyl fluid, the mixture heated to 85° when 0.5 cc tetrabutyltitanate were added, with the complete reaction blend refluxed at 118° for 18 hours. 2 cc H₂O were added to hydrolyze the titanate before stripping the mixture at 115°, 10 mm vacuum. The final product was a 1320 cps fluid, $N^D = 1.5046$, with infrared spectrum consistent with the anticipated transesterification product.

The resultant polysiloxane was acrylic end-capped and acrylic on chain joined through a thioether link.

Example 3

A non-devolatilized silicone polymer was prepared by KOH-equilibration of $D_4$, $D_4^{Vi}$ and vinyl chainstopper to furnish a 190 cps fluid bearing approximately 0.08 moles vinyl function per 100 grams polymer, $N_{25}^D = 1.4095$. 300 grams of this fluid were dispersed in 300 grams toluene with 21 grams mercaptoethanol (0.27 moles) +0.6 gram Vazo ® 88 initiator. This mixture was agitated at 100° C. under nitrogen for 17 hours, then stripped at 160°, 20 mm vacuum. 301 grams of a viscous fluid product were obtained, $N_{25}^D = 1.4165$, the infrared spectrum of which included a broad —OH absorption at 3400 cm⁻¹. This fluid was transesterified by an excess of ethyl acrylate using tetrabutyltitanate as transesterification catalyst in a manner analagous to Example 2. The final product was a devolatilized 765 cps fluid displaying a strong carbonyl band at 1730 cm⁻¹ in the infrared, 279 grams yield, $N_{25}^D = 1.4180$. The resultant polysiloxane was acrylic end-capped and acrylic on chain joined through a thioether link.

Example 4

Qualitative UV-curing performance of these experimental coating mixtures consisting of mixtures of these photoactive silicone polymers with photoinitiators was established by depositing various thicknesses of the blends onto several different substrates, then exposing the coatings to ultraviolet radiation supplied by two focused Hanovia medium pressure mercury lamps mounted above a moving conveyor belt housed in a PPG model QC 1202 UV Processor. Each lamp is independently capable of operation at 100, 200, or 300 watts/inch power. Cure was assessed as a function of total lamp power and conveyor line speed. Actual ultraviolet flux can be estimated by comparison with a measured average radiation flux of 1.5 Joules/cm² at 400 watts/in (focused) total lamp power with a 20 feet/min. line speed. Results are presented in Table I. The following abbreviations apply.

SCK: 40 #1 ream supercalendered Kraft paper
D-1173: Darocure ® 1173 photoinitiator, 2,2-dimethyl-2-hydroxyacetophenone, EM Chemicals
Al: 25 mil aluminum Q panel

TABLE I

| Comp. Examples | Photoinitiator 4 wt % | Substrate | Thickness mil | Lamp Power, Watt | Atmosphere | Line Speed | Observation |
|---|---|---|---|---|---|---|---|
| 1 | D-1173 | SCK | 2 | 400 | inert | 100 | Cured - no migration |
| 1 | D-1173 | SCK | 2 | 400 | inert | 200 | Undercured-slight smear |
| 1 | D-1173 | SCK | 2 | 600 | air | 50 | Cured - poor anchorage |
| 2 | D-1173 | SCK | 2 | 400 | inert | 200 | Cured - no smear |
| 2 | D-1173 | SCK | 2 | 400 | inert | 400 | Undercured-slight smear |
| 2 | D-1173 | Al | 5 | 600 | inert | 200 | Cured - no smear |
| 2 | D-1173 | SCK | 2 | 600 | air | 50 | Cured - no smear |
| 2 | D-1173 | SCK | 2 | 600 | air | 100 | Poor cure - smear |
| 3 | D-1173 | SCK | 2 | 400 | inert | 200 | Cured - no migration, good anchorage |
| 3 | D-1173 | SCK | 2 | 400 | inert | 400 | Cured - no migration, rubs off |
| 3 | D-1173 | SCK | 1 | 600 | air | 50 | Cured - no smear, good anchorage |
| 3 | D-1173 | SCK | 1 | 600 | air | 100 | Cured - slight smear, good anchorage |
| 3 | D-1173 | SCK | 1 | 600 | air | 150 | Undercured - smears |
| 3 | D-1173 | Al | 5 | 600 | air | 100 | Cured slight smear |

The polymers of examples 1 to 3 are curable by ultraviolet irradiation in the presence of standard photoinitiators which, along with their respective infrared spectra and changes in refractive indices, serves as further evidence that these polymers are in fact acryloxyethyl-thioether-functional silicones as proposed. Acrylated silicones prepared in this laboratory by other means (which do not incorporate thioether linkages) typically display very sluggish UV cure response in the presence of oxygen; it was therefore surprising to find that the thioether-bridged acrylic silicones show fairly good UV cure response in the presence of atmospheric oxygen.

Example 5

200 grams of the $M^{Vi}D_{20}M^{Vi}$ polymer ($N_{25}^D = 1.4035$) used to make the acrylated polymer in example 1 were dispersed in 200 grams toluene with 27 grams of 3-mercaptopropionic acid +0.6 gram Vazo ® 88 radical catalyst. This reaction mixture was maintained at 100° under nitrogen for 4 hours. Stripping off solvent and excess mercaptopropionic acid at 160°, 30 mm vacuum left 210 grams of a 122 cps. fluid, $N_{25}^D = 1.4233$. The infrared spectrum of this polymer included a broad —OH peak centered at 3000 cm⁻¹ and a strong carbonyl peak at 1710 cm⁻¹. 100 grams of the carboxylic acid-functional fluid were then reacted with 12 grams beta-mercaptoethanol using 200 grams toluene as solvent, and 2 cc tetrabutyl-titanate as esterification catalyst. 2.6 cc water was trapped out in a Dean-Stark apparatus following three hours reflux at 140° C. The reaction product was ultimately isolated as a 62 cps fluid, $N_{25}^D = 1.4310$. Loss of —OH stretch coupled with retention of C=O stretch in the product infrared spectrum helps to confirm the nature of the product as a polysiloxane having mercaptan functionality joined through a thioether linkage.

Example 6

A 1:1 by weight blend of the acrylic functional polysiloxane from example 3 and the mercaptan functional polysiloxane from example 5 were combined with 5% by weight D-1173 and applied to a thickness of 2 mil to an SCK substrate. The coating was cured by exposure to 600 watts/in total focused UV light at 200 ft/min line speed in air. The coating was cured to a smear-free surface which released #610 Scotch ® cellophane tape.

What is claimed is:

1. A UV active silicone compound comprising UV active moieties of the formula:

$$\equiv Si-R_a-CHR^1-CR^1H-S-R-X^1-R-Z$$

where R is a divalent hydrocarbon radical of from 1 to 12 carbon atoms; $X^1$ is —COO— or —OOC—; $R^1$ is —H or an alkyl group of from 1 to 4 carbon atoms; a is 0 or 1, and Z is —SH.

2. The compound of claim 1 wherein said UV active silicon compound is a silane.

3. The compound of claim 1 wherein said UV active silicon compound is a siloxane or polysiloxane.

4. The compound of claim 3 wherein said polysiloxane has a viscosity between about 5 and 100,000,000 centipoise at 25° C. and comprises units of the formula:

$$R_d^2 SiO_{(4-d)/2}$$

wherein d is 0, 1, 2, or 3, and $R^2$ is hydrogen or a monovalent hydrocarbon radical of from 1 to 12 carbon atoms.

5. The compound of claim 4 wherein said polysiloxane contains at least two said UV active moieties.

6. The compound of claim 4 wherein said polysiloxane contains UV active moieties by weight equivalent to from about 0.1 to about 10% by weight of siloxane bonded unsaturated hydrocarbons.

7. The compound of claim 1 wherein a is 0 and $R^1$ is hydrogen.

* * * * *